United States Patent [19]

Roos

[11] 4,319,493
[45] Mar. 16, 1982

[54] APPARATUS FOR INSERTING A THREAD INTO A TESTING POSITION OF A TENSILE STRENGTH TESTING APPARATUS

[75] Inventor: Gerold Roos, Esslingen, Switzerland

[73] Assignee: Zellweger, Ltd., Esslingen, Switzerland

[21] Appl. No.: 167,027

[22] Filed: Jul. 9, 1980

[30] Foreign Application Priority Data

Sep. 19, 1979 [CH] Switzerland ............... 8441/79

[51] Int. Cl.³ ............................................. G01N 3/08
[52] U.S. Cl. ..................................................... 73/828
[58] Field of Search ................ 73/828, 830, 831, 789, 73/855, 856

[56] References Cited

U.S. PATENT DOCUMENTS 2,037,273 4/1936 Scott ..................................... 73/831

*Primary Examiner*—Anthony V. Ciarlante
*Attorney, Agent, or Firm*—Craig and Antonelli

[57] ABSTRACT

An apparatus for inserting a thread between the testing clamps of a tensile strength testing apparatus has an insertion clamp which can travel vertically on a slide movable on a vertical rail which is also movable horizontally, whereby movement of the insertion clamp in orthogonal directions is possible. An automatic control mechanism is operable to command a drive arrangement for the insertion clamp to move the clamp along any desirable path which carries the thread to the required position in the testing apparatus.

8 Claims, 2 Drawing Figures

APPARATUS FOR INSERTING A THREAD INTO A TESTING POSITION OF A TENSILE STRENGTH TESTING APPARATUS

BACKGROUND OF THE INVENTION

The present invention relates to an apparatus for inserting a thread into a testing position of a tensile strength testing apparatus.

Automatic tensile strength testing apparatus require a mechanism operable automatically to insert the thread to be tested between clamps in a testing frame, that is, for a predetermined number of tensile strength tests.

For this purpose, a known tensile strength testing apparatus has, for example, a rotatable and translatory movable insertion arm carrying a clamp which catches the thread at a predetermined point and which moves along a path which is so oriented that the clamp holding the thread inserts the trailing end of the thread between opened testing clamps. However, such movements of this type of insertion arm require a considerable amount of space and also interfere with the operation of the apparatus because of the movement of the arm which swings back to a great extent.

Other known constructions comprise an endless movable chain with a gripper which catches a prepared thread and inserts it between testing clamps. However, an arrangement of this type can only be used in specific cases, namely, when the testing frame including the testing clamp, is not at the front of the apparatus, as a movable chain would then be an obstacle. Both types of known apparatus also have the disadvantage that the path of movement of the clamp or gripper holding the thread cannot be set towards any random point or be caused to move selectively along any desired path.

The present invention seeks to avoid these disadvantages and provides an apparatus for inserting a thread into the testing position of a tensile strength testing apparatus, whereby at least one thread is maintained ready in a clamping device, the said apparatus comprising an insertion clamp which is vertically movable along a rail which is itself movable to and fro in a horizontal direction in front of the tensile strength testing apparatus by means of a traveling mechanism, thereby permitting unlimited orthogonal movement of the insertion clamp along any desired path.

The insertion apparatus according to the invention provides a number of advantages which either cannot be achieved by known methods or can only be achieved at considerable expense, namely:

(1) there may be different clamping lengths between testing clamps in different installations, but the invention provides the shortest path in each case for the insertion clamp to thereby optimize the operating speed for each installation;

(2) the insertion rate can be controlled in accordance with the invention by superimposing horizontal and vertical movement of the insertion clamp, so that abrupt changes in direction by a slide carrying the insertion clamp may be particularly avoided;

(3) the insertion clamp may, for example, be moved in a circular manner or in a wavy manner, so that it can wind the thread around bolts or position the thread around bolts in a zig-zag line; and (4) the remainder of the thread may be fed into a suction nozzle while the insertion clamp is passed by such a nozzle.

BRIEF DESCRIPTION OF THE DRAWING

One embodiment of the invention will now be described with reference to the accompanying drawing, in which.

DESCRIPTION OF THE PREFERRED EMBODIMENT

Figure 1:
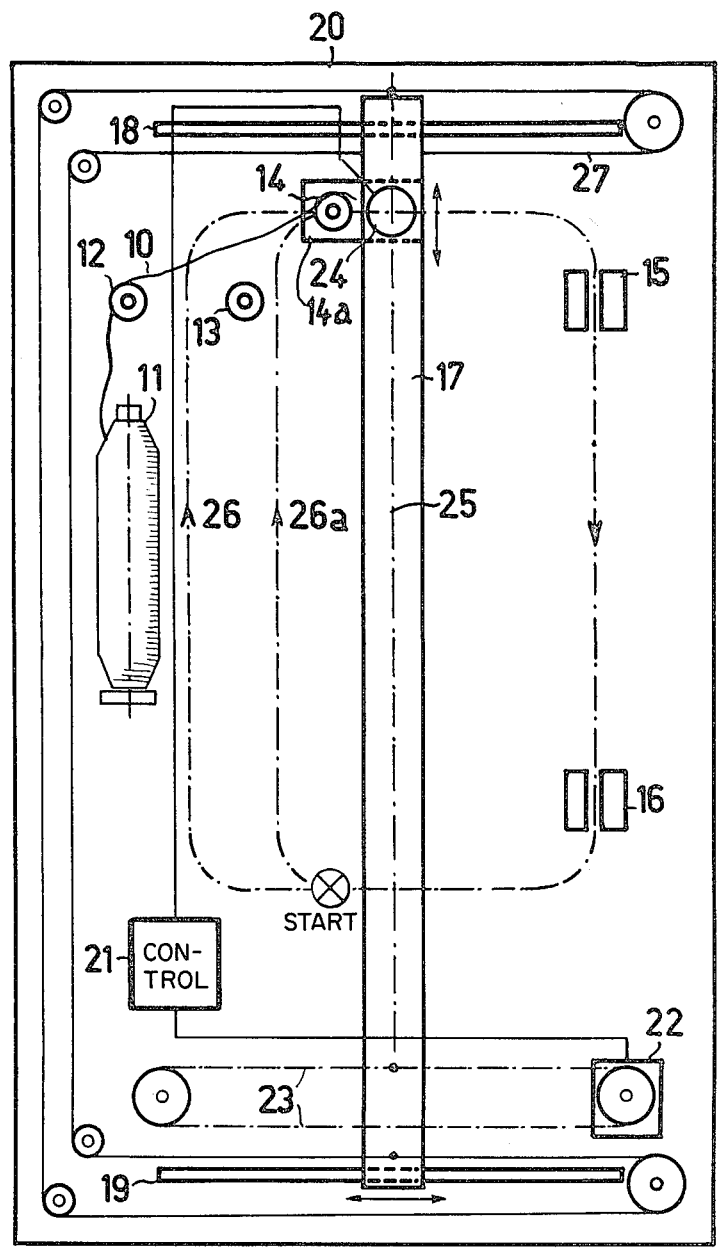
FIG. 1 is a schematic front view of a tensile strength testing apparatus including the present invention.

The drawing schematically illustrates a tensile strength testing apparatus 20 which comprises testing clamps 15 and 16 between which a thread 10 is inserted, clamped and subjected to an increasing stress, for example in accordance with the method disclosed in the Brassel et al U.S. application Ser. No. 164,941, filed July 1, 1980, assigned to the same assignee as the present application. As such tensile tests are to a great extent carried out in a successive or repeated manner, an automatic testing procedure is provided to relieve the operating staff from having to insert the thread 10 between the clamps 15,16 and also to shorten the testing time.

The thread 10 to be tested is first inserted into a clamping device formed by clamping eyelets 12 and 13. The thread can either be removed from a single bobbin 11 (as illustrated), or alternatively, threads can be automatically selected from a plurality of bobbins so that a representative average of the measuring values is obtained. Since the automatic bobbin changing device associated with this apparatus does not directly affect the present invention, it is not explained herein in detail.

The apparatus comprises an insertion clamp 14 which can travel with a slide 14a in two directions—horizontally and vertically—in front of a front panel of the testing apparatus 20. For this purpose, the slide 14a can be moved up and down on a rail 17 by means of a vertical drive means 24. For this purpose, the rail 17 may have a toothed channel in which there is engaged a pinion gear carried by the slide 14a. The drive means 24 in the form of a reversible motor drives the pinion gear under control of a control device 21 to move the slide up and down vertically on the rail 17. The rail 17 can be moved laterally as a whole in a horizontal direction guided by the traveling mechanism made up of guides 18 and 19. A horizontal drive means 22 transfers movement commands delivered by the control device 21 to the rail 17 by means of a cable, cord, chain or toothed belt 23 which is secured to the rail. Thus, by suitable control from the control device 21, the insertion clamp 14 can be moved according to a given program along a selected path which passes between the clamping eyelets 12,13 and the testing clamps 15,16.

In order to guide the rail 17 while maintaining its vertical disposition exactly, a mechanical connection, for example, a cord 27 is advantageously connected to the rail 17 in the region of the upper and lower horizontal traveling guides 18,19, the cord 27 extending over a suitable roller guide arrangement for positively conveying the rail 17. In this way the top and bottom of rail 17 are linked together for coordinate movement back and forth along guides 18,19 under the driving force supplied by drive means 22.

Figure 2:
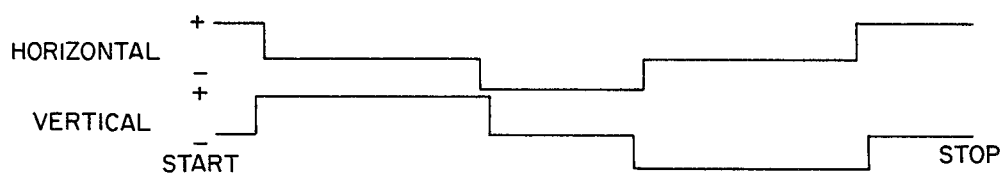
FIG. 2 is a waveform diagram of control signal waveforms applicable to the system of FIG. 1.

The control device 21 may be provided in any known form to effect single cycle operation controlled from the tensile strength testing apparatus. Thus, the device 21 may be provided in the form of a simple pattern signal generator capable of providing control signals such as seen in FIG. 2 upon receipt of a start signal from the testing apparatus. However, the present invention is not limited to the type of control provided, but is compatible with various types of control arrangements for effecting different patterns of thread insertion.

In operation, when the insertion clamp 14 moves from the start position and passes the thread 10 lying ready between the clamping eyelets 12 and 13, the thread 10 is caught and inserted between the testing clamps 15 and 16 along the path 26 indicated by the arrows in FIG. 1. If the insertion operation is repeated from the same bobbin, the clamp 14 can also be controlled by the control device 21 to move along a shorter insertion path 26a with the advantage of a shorter insertion time, as well as keeping a bobbin changer free for its operation.

As the insertion claim 14 returns to the start position, it is opened outside the lower testing clamp 16, and the testing clamps 15 and 16 are closed whereupon the actual tensile operation may be started.

While I have shown and described one exemplary embodiment in accordance with the present invention, it is understood that the same is not limited thereto but is susceptible of numerous changes and modifications as are obvious to one of ordinary skill in the art, and I therefore do not wish to be limited to the details shown and described herein but intend to cover all such changes and modifications obvious to those skilled in the art.

What is claimed is:

1. An apparatus for inserting a thread into the testing position of a tensile strength testing apparatus, in which at least one thread is maintained in a ready position in a clamping device for insertion, the said apparatus comprising an insertion clamp; means including a rail for mounting said insertion clamp for movement oriented in a first direction along said rail in the vicinity of the tensile strength testing apparatus; means for moving said rail in a second direction orthogonal to said first direction; and traveling guide means connected to said rail for maintaining the orientation thereof in said first direction while said rail is moved in said second direction.

2. An apparatus according to claim 1, wherein the means for moving the rail includes a drawing member in the form of an endless drive member.

3. An apparatus according to claim 2, wherein said drawing member is a cord attached to said rail.

4. An apparatus according to claim 2, wherein said drawing member is a chain attached to said rail.

5. An apparatus according to claim 2, wherein said drawing member is a toothed belt attached to said rail.

6. An apparatus according to claim 1 or claim 2, wherein said testing apparatus includes an upper testing clamp, and including automatic control means operable to determine the path of the insertion clamp in such a way that it moves from a starting position to catch the thread at the clamping device, inserts in first into the open upper testing clamp, and then into the open lower testing clamp, releases the thread after the testing clamps have been closed and returns to the starting position.

7. An apparatus according to claim 6, wherein said automatic control means includes means operable to move the insertion clamp along alternative paths to within a surface bounded by the rail and the traveling guide means.

8. An apparatus according to claim 1, wherein said traveling guide means includes an endless band and a roller guide arrangement for guiding said endless band along a path which includes portions extending in said second direction at the upper and lower ends of said rail and secured to said rail at said ends so as to effect conjoint movement of the ends of said rail in said second direction.

* * * * *